US008846306B2

(12) United States Patent
Zal et al.

(10) Patent No.: US 8,846,306 B2
(45) Date of Patent: Sep. 30, 2014

(54) **USE OF A GLOBIN, A GLOBIN PROTOMER OR AN EXTRACELLULAR HEMOGLOBIN OBTAINED FROM THE MARINE WORM, *ARENICOLA MARINA*, FOR THE PRESERVATION OF ORGANS, TISSUES, CELLS OR CELL CULTURES**

(75) Inventors: Franck Zal, Ploujean-Morlaix (FR); Morgane Rousselot, Saint Pol de Leon (FR); Delphine Dutheil, Saint Julien l'Ars (FR)

(73) Assignees: Hemarina SA, Morlaix Cedex (FR); Centre National de la Recherche Scientifique, Paris Cedex (FR); Universite Pierre et Marie Curie (Paris 6), Paris (FR)

( * ) Notice: Subject to any disclaimer, the term of this patent is extended or adjusted under 35 U.S.C. 154(b) by 189 days.

(21) Appl. No.: 12/672,610

(22) PCT Filed: Jul. 25, 2008

(86) PCT No.: PCT/FR2008/001116
§ 371 (c)(1),
(2), (4) Date: Feb. 8, 2010

(87) PCT Pub. No.: WO2009/050343
PCT Pub. Date: Apr. 23, 2009

(65) Prior Publication Data
US 2010/0209902 A1 Aug. 19, 2010

(51) Int. Cl.
*A01N 1/02* (2006.01)
*C12N 5/00* (2006.01)
*A61K 38/42* (2006.01)

(52) U.S. Cl.
CPC ............ *A01N 1/0226* (2013.01); *C12N 5/0037* (2013.01); *A61K 38/42* (2013.01)
USPC ......................................................... 435/1.1

(58) Field of Classification Search
CPC ..... A01N 1/0226; C12N 5/0037; A61K 38/42
See application file for complete search history.

(56) References Cited

U.S. PATENT DOCUMENTS

| | | | |
|---|---|---|---|
| 6,673,594 B1 * | 1/2004 | Owen et al. ................ | 435/284.1 |
| 7,220,538 B2 | 5/2007 | Fischer et al. | |
| 2003/0181358 A1 * | 9/2003 | Zal et al. ........................ | 514/6 |

FOREIGN PATENT DOCUMENTS

| | | |
|---|---|---|
| DE | 102 20 990 | 11/2003 |
| FR | 2 860 796 | 4/2005 |
| WO | 00/18226 | 4/2000 |
| WO | 01/02320 | 12/2001 |
| WO | 01/92320 | 12/2001 |
| WO | 02/089571 | 11/2002 |
| WO | WO 2006/052133 A2 * | 5/2006 |
| WO | 2007/085596 | 8/2007 |

OTHER PUBLICATIONS

Hirsch et al., "A first evaluation of the natural high molecular weight polymer *Lumbricus terrestris* hemoglobin as an oxygen carrier", Artificial Cells, Blood Substitutes and Immobilization Biotechnology 25 (5) : 429-444 (1997).*
Frietsch et al., "Artificail oxygen carriers", European J. Anaesthesiology 15 : 571-584 (1998).*
Sullivan et al., "Targeted Oxygen Delivery within Hepatic Hollow Fiber Bioreactors via Supplementation of Hemoglobin-Based Oxygen Carriers", Biotechnol. Prog. 22 : 1374-1387 (2006).*
Jewitt et al., "Oxygenated perfluorocarbon promotes nematode growth and stress-sensitivity in a two-phase liquid culture system", Enzyme and Microbial Technology 25 : 349-356 (1999).*
Dinkelmann et al., "A system establishing compatibility profiles for artificial oxygen carriers and other substances", Artificial Cells, Blood Substitutes and Immobilization Biotechnology 29 (1) : 57-70 (2001).*
Ortegon et al., "The Polymerized Bovine Hemoglobin-Based Oxygen-Carrying Solution (HBOC-201) Is Not Toxic to Neural CElls in Culture", J. Trauma 53 : 1068-1072 (2002).*
Harrington et al., "Acellular Invertebrate Hemoglobins as Model Therapeutic Oxygen Carriers: Unique Redox Potentials", Artificial Cells, Blood Substitutes and Biotechnology 35 (1) : 53-67 (2007).*
French Search Report in FR 07 05804, dated May 20, 2008.
Rousselot et al., Biotechnol. J., 1(3):333-345 (2006).
Pionetti et al., Eur. J. Biochem., 105(1):131-138 (1980).
Thuillier, R. et al., Am J Transplantation (2011) 11:1845-1860.

* cited by examiner

*Primary Examiner* — Sandra Saucier
(74) *Attorney, Agent, or Firm* — McAndrews, Held & Malloy Ltd.

(57) ABSTRACT

The invention relates to the use of at least one globin and/or at least one globin protomer and/or at least one naturally extracellular native hemoglobin for the preservation of organs, tissues, organ and tissue cells and cell cultures.

16 Claims, 4 Drawing Sheets

Figure 1:
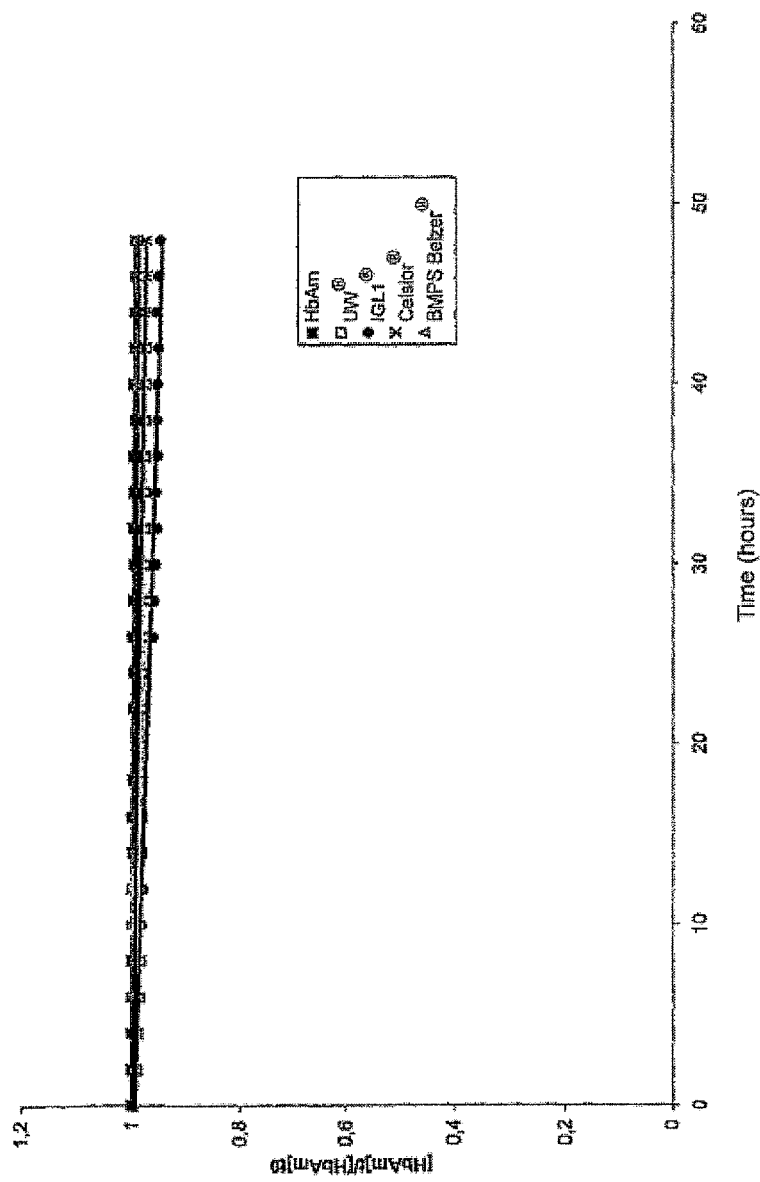

USE OF A GLOBIN, A GLOBIN PROTOMER OR AN EXTRACELLULAR HEMOGLOBIN OBTAINED FROM THE MARINE WORM, *ARENICOLA MARINA*, FOR THE PRESERVATION OF ORGANS, TISSUES, CELLS OR CELL CULTURES

The present application is filed pursuant to 35 U.S.C. 371 as a U.S. National Phase application of International Patent Application No. PCT/FR08/01116, which was filed Jul. 25, 2008, claiming the benefit of priority to French Patent Application No. 07/05,804, which was filed on Aug. 9, 2007. The entire text of the aforementioned applications is incorporated herein by reference in its entirety.

The present invention relates to the use of at least one globin and/or at least one globin protomer and/or at least one naturally extracellular native hemoglobin for the preservation of organs, tissues, or organ or tissue or cell culture.

The Annelids have been much studied on account of their extracellular hemoglobin (N. B. Terwilliger, *Molecular structure of the extracellular heme proteins*, Vol. 13, C. P. Mangum (Ed.), 193-229, Springer-Verlag, Berlin (1992); J. N. Lamy, B. N. Green, A. Toulmond, J. S. Wall, R. E. Weber and S. N. Vinogradov, Chem. Rev. 96 3113-3124 (1996)). These molecules of extracellular hemoglobin are present in the three classes of Annelids: Polychetes, Oligochetes and Achetes and even in the Vestimentifera which have recently become the family of the siboniglidae, included in the Polychetes class. These are giant biopolymers, made up of about 200 polypeptide chains of 6 or 8 different types which are generally grouped into two categories. The first category, with 144 to 192 components, groups the so-called "functional" polypeptide chains, bearing an active site and capable of reversibly binding oxygen; these are chains of the globin type the masses whereof lie between 15 and 18 kDa and which are very similar to the α and β type chains of vertebrates. The second category, with 36 to 42 components, groups the so-called "structural" polypeptide chains having little or no active site but enabling assembly of the twelfths.

The first images obtained for *Arenicola* extracellular hemoglobins (J. Roche, M. Bessis and J. P. Thiery, Biochim. Biophys. Acta 41 182-184 (1960); J. Roche, M. T. Bessis and J. P. Thiery, C. R. Soc. Biol. 154 73-80 (1960)) revealed hexagonal components. Each molecule of hemoglobin is made up of two superposed hexagons (O. Levin, J. Mol. Biol. 6 95-101 (1963); J. Roche, *Electron microscope studies on high molecular weight erythrocruorins (invertebrate hemoglobins) and chloro-cruorins of annelids*, D. A. Munday (Ed), 62-80, Pergamon Press, Oxford (1965)) which were called the hexagonal bilayer and each hexagon is itself formed by the assembly of six components in the shape of a drop of water (E. F. J. Van Bruggen and R. E. Weber, Biochim. Biophys. Acta 359 210-212 (1974); O. H. Kapp and A. V. Crewe, Biochim. Biophys. Acta 789 294-301 (1984), called the hollow globular structure (F. De Haas, F. Zal, V. You, F. H. Lallier, A. Toulmond and J. N. Lamy, J. Mol. Biol. 264 111-120 (1996); F. De Haas, F. Zal, F. H. Lallier, A. Toulmond and J. N. Lamy, Proteins—structure function and genetics, 3 241-256 (1996); F. De Haas, N. Boisset, J. C. Taveau, O. Lambert, S. N. Vinogradov and J. N. Lamy, Biophys. J. 70 1973-1984 (1996)) or "twelfth". The native molecule is formed of twelve of these subunits (dodecamer), with a molecular mass lying between 200 and 250 kDa which constitutes the functional unit of the native molecule.

There is particular interest in *Arenicola marina*, a Polychete Annelid of the intertidal ecosystem. Moreover the structure of its extracellular hemoglobin is already known (F. Zal, B. N. Green, F. H. Lallier, S. N. Vinogradov and A. Toulmond, Eur. J. Biochem. 243 85-92 (1997)).

Organ transplantation consists of replacing a diseased organ in a patient with a healthy organ, referred to as the transplant, and derived from a donor.

The distribution of oxygen to all the organs and tissues in the human body is ensured by the hemoglobin present in the human or animal bloodstream.

After removal from the donor, the organ is no longer supplied with oxygen and hence during the process of organ transplantation keeping the organ alive for as long as possible outside the body during the time that separates the removal from the donor to implantation in the patient is indispensible to the success of the transplant and involves the development of storage methods.

After explantation, the transplant is deprived of its physiological environment and thus becomes very sensitive. In normothermia (37° C.), interruption of the vascularization of an organ results in rapid necrosis of the cells constituting it. The organ preservation solution intervenes to protect it. One of the great principles of organ preservation is to decrease its temperature rapidly from 37° C. to 4° C. In fact, decreasing the temperature of the tissues results in a decrease in the cell metabolism, without however stopping it (Belzer F. O., Southard J. H., Principles of solid organ preservation by cold storage. Transplantation 1988; 45(4): 673-676). Hypothermia and the composition of the storage solution make it possible to combat the deleterious effects of oxygen and nutrient deprivation induced by the stoppage of the blood circulation and defer the death of the cells, which is responsible for necrosis of the tissues. Thus, owing to its osmotic and/or antioxidant properties, the solution contributes to the maintenance of the quality and the integrity of the transplant (morphology and biochemistry). In particular, it maintains its viability ex vivo:

during the removal phase, the transplant will be perfused with the preservation solution in order to rinse it and free it from the donor's blood ("rinse solution"). The organ is cooled following hypothermic perfusion performed ex vivo or in situ depending on whether it is being removed from a living donor or a cadaver. The washing also serves to equilibrate the organ with the components of the solution.

the period from the start of explantation from the donor up to the end of the implantation into the recipient is critical: it is the period of total ischemia. This stage is the cause of many observed deleterious effects. Ischemia can be defined as an insufficiency of tissue blood supply, with the loss of three important functions of the bloodstream: supply of nutrients, oxygenation and elimination of wastes.

A distinction is made between the warm ischemia period: the period when the organ is no longer perfused with the donor's blood but not yet refrigerated, and the cold ischemia period: the period after washing and refrigeration of the organ up to its revascularization in the recipient. After the organ has been rewarmed and before perfusion with the recipient's blood, a period of secondary warm ischemia can be observed. The preservation solution has a real role in protecting the transplant during transport ("holding solution").

Hypothermia is the essential component of storage. It reduces the tissue metabolism, in other words it slows the catalytic enzymatic activity necessary for cell viability. The metabolism is said to be decreased from 12 to 13-fold when the temperature passes from 37° C. to 0° C. (Belzer and Southard, Principles of solid organ preservation by cold storage. Transplantation 1988; 45(4): 673-676 (1988)).

It is in fact necessary to reduce the transplant's oxygen and energy demand and consumption, since it is in a state of ischemia. This implies that the tissue is deprived of oxygen. Hence the synthesis of energy in the form of ATP is no longer ensured by oxidative phosphorylation but by anaerobic glycolysis the yield whereof is very much lower. Ischemic tissue has almost no energy reserve and deteriorates rapidly.

It is thus important to reduce its needs using hypothermia. The quality of the cold storage (ca 4° C.) will determine the success of the reperfusion after implantation. The organ is simply immersed into the solution maintained at low temperature with crushed ice under conditions of guaranteed asepsis: static storage in the cold.

The acceptable time for ensuring the transplant's subsequent resumption of function varies from one organ to another. For example, it is about 4-5 hours for the heart, 4-6 hours for the lung, 6 hours for the intestine, 10-16 hours for the liver, 24-35 hours for the kidney and 12-18 hours for the pancreas (thesis by Melle Delphine FORNAS defended on 15 Jun. 2001: Organ preservation solution: specification, regulatory status and registration in Europe; Université Claude Bernard—Lyon I; Faculty of Pharmacy; Institute of Pharmaceutical and Biological Sciences).

Consequently, the development of storage methods has in particular been studied.

Thus, the U.S. Pat. No. 7,220,538 relates to a composition for preservation of organs or cells, with two phases, comprising a first phase which contains a nutrient base medium and a second phase which contains nanoparticles containing a solution or suspension with a component capable of binding or supplying oxygen which can be hemolyzed and chemically modified intracellular hemoglobin. This solution is maintained at a non-hypothermic temperature of about 20 to 37° C.

The U.S. Pat. No. 6,994,654 relates to a solution for preservation of organ and tissues which contains a solution based on electrolytes with a high potassium content and an additive which can be PEG-hemoglobin for a process of provision, preservation, transplantation and/or non-hemorrhagic surgery involving an organ or a tissue. It is stated that the molecules transporting oxygen, used as an additive, are used for "normothermic" perfusion. When the perfusion is hypothermic, no oxygen transporter is present since at hypothermic temperatures the hemoglobin of vertebrates from which the molecule described in this patent is derived does not have the same functional properties as at 37° C., in particular its affinity for oxygen, since the affinity of hemoglobin for oxygen depends on the temperature.

The patent application US 2006/0063142 relates to an apparatus and a process for organ perfusion for the monitoring, maintenance and/or restoration of organs and the preservation of organs during holding or transport.

The process comprises the perfusion of an organ with a first medical fluid at a first temperature (preferably higher than 25° C.) which can contain an oxygen transporter such as red cells or crosslinked hemoglobin, after rinsing with a solution which can be VIASPAN™ or other colloidal solutions containing dextran or HES (hydroxyethyl starch) or other equivalent compounds, then the perfusion of the organ with a second medical fluid which does not contain oxygen at a second temperature (preferably lying between 4 and 10° C.) lower than the first.

The U.S. Pat. No. 6,642,045 relates to a metabolic support system comprising an organ or a tissue which uses a perfusion solution which can contain an oxygen transporter such as hemoglobin, a stabilized hemoglobin, polyoxyethylene conjugates of hemoglobin or a recombinant hemoglobin. The use temperature of the system lies between 25 and 37° C.

The application WO 01/01774 relates to a composition for the preservation of organs for transplantation containing a bovine PEG-hemoglobin, one or more essential electrolytes, at least one soluble protein, at least one nutrient formulation and at least one agent acting on the cardiovascular system.

In these different documents, the hemoglobin used is of human or mammalian origin and is either in the red cells, or in liposomes, or else it is crosslinked or bridged with polyethylene glycol (PEG-hemoglobin) to avoid oxidation as it is well known that when a hemoglobin is isolated from a red cell this will be oxidized owing to the absence of the antioxidant activity of the enzymes present in the red cell (Savitsky J P, Doczi J, Black J and Arnold J D (1978) A clinical safety trial of stroma-free hemoglobin. Clin Pharmacol Ther 23, 73-80), (Chan W L, Tang N L, Yim C C, Lai F M and Tam M S (2000); New features of renal lesion induced by stroma-free hemoglobin, Toxicol Pathol 28, 635-642). The use of red cells also necessitates the control of the osmotic pressure. Beyond 289 mOsMoles (normal osmotic pressure of the red cell), the red cell will be in a hyperosmotic medium and will have a tendency to lose the water which it contains. This physical process disturbs the membrane exchanges, in particular the sodium/chlorine exchanges (Hendry E B (1961) Osmolarity of human serum and chemical solution of biological importance. Clin. Chem., 2, 156-164).

Likewise, the use of a human or mammalian hemoglobin only allows normothermic temperatures for organ preservation since beyond these the functioning of the red cell is severely disrupted (Jensen F B, Wang T, Brahm J, 2001, Acute and chronic influence of temperature on red blood cell anion exchange, 204, 39-45). Moreover, the use of a hemoglobin from vertebrates makes it necessary to know the blood type of the donor and the recipient in order to avoid an immunological reaction (Goodnough, Clin Orthop Relat Res. 1998 December; (357) 89-100).

However, improvement of the survival of the transplant during ischemia for a longer period will enable better study of the immunology and of the operating conditions, thus favoring the success of the transplant.

Similarly, improvement of the oxygenation of the transplant and hence of its quality will enable a more rapid resumption of function.

Consequently, one of the objectives of the invention is to provide globins and/or globin protomers and/or extracellular hemoglobins in combination with a medium for organ or cell culture storage making it possible to produce a composition for preservation of organs, tissues, or organ or tissue cells or cell culture.

Another objective of the invention is to provide a composition for preservation of organs, tissues, or organ or tissue cells or cell culture not necessitating blood typing.

Another aspect of the invention is to provide a composition for preservation of organs, tissues, or organ or tissue cells or cell culture enabling prolonged use over time and capable of functioning at a hypothermic temperature.

Another aspect of the invention is to provide a cell culture composition capable of functioning at a hypothermic temperature.

Another objective of the invention is to provide a composition containing at least one globin and/or at least one globin protomer and/or at least one extracellular hemoglobin in an organ storage medium enabling the preservation of organs, tissues, or organ or tissue cells or cell culture.

Another objective of the invention is to provide a process for storage of organs, tissues or organ or tissue cells.

Another aspect of the invention is to provide a process for organ perfusion.

Another objective of the invention is to provide a process for cell culture.

Consequently, the invention relates to the use of at least one globin and/or at least one globin protomer and/or at least one naturally extracellular native hemoglobin of an invertebrate animal selected from the phylum of the annelids and in particular at least one globin and/or at least one globin protomer and/or at least one extracellular hemoglobin belonging to marine worms such as *Arenicola marina*, at a concentration lying between about 0.625 mg/ml to about 100 mg/ml preferably about 0.625 mg/ml to about 20 mg/ml, more preferably about 0.625 mg/ml to about 5 mg/ml in particular 1.25 mg/ml, relative to the final volume, in combination with an organ storage medium, or a cell culture medium, for the production of a composition for preservation of organs, tissues, or organ or tissue cells, or for perfusion of organs or tissues or for cell culture.

"Globin protomer" is understood to mean the twelfth or the dodecamer of the globin.

"Native" is understood to mean a globin, or a globin protomer or a hemoglobin originating from said invertebrate animal.

"Naturally extracellular" is understood to mean a globin, or a globin protomer or a hemoglobin which is naturally not contained in a cell and can thus circulate freely in the circulatory system without chemical modification to stabilize it and render it functional.

The extracellular hemoglobin of *Arenicola marina* is a giant bipolymer of mass about 3 to 4 million daltons and made up of about 200 polypeptide chains of two types. Three quarters are chains of the globin type capable of reversibly binding oxygen ($O_2$) and the remaining quarter are structural chains ("linkers") which ensure the maintenance of the quaternary structure and are thought to be responsible for the antioxidant activity of this molecule. The functional unit of this molecule is the dodecamer which has a mass lying between 200 and 250 kDa.

Consequently, the invertebrate animal extracellular hemoglobin or globin protomer or globin can consist of a single polypeptide chain up to about several hundreds of polypeptide chains, say a molecular weight lying between about 15,000 daltons to about 8 million daltons.

The use of at least one globin and/or at least one globin protomer and/or at least one extracellular native hemoglobin makes it possible to exploit the intrinsic superoxide dismutase (SOD) activity (determined by the method of Flohé and Ötting; Flohé L, Ötting F. Methods Enzymol (1984), 105, 93-104) of said hemoglobin or globin or globin protomer, thus obtaining an intrinsic antioxidant activity and consequently not requiring any antioxidant in order to function, in contrast to the use of a mammalian hemoglobin for which the anti-oxidant molecules are contained in the interior of the red cell and are not bound to the hemoglobin. On the other hand, the globin or globin protomer or extracellular hemoglobin do not require a cofactor to function, unlike mammalian, in particular human, hemoglobin.

Invertebrate animal is understood to mean an animal which has no vertebral column such as the medusae, sponges, insects, crustaceans, mollusks, etc., or an animal which belongs to the annelid phylum.

The hemoglobin concentration in the marine worm *Arenicola marina* lies between 100 and 170 g/l of blood (Toulmond A. (1975). Studies on the respiratory physiology of the polychete annelid *Arenicola marina* (L.). D. Sc. thesis, Pierre-et-Marie-Curie (Paris VI), Paris) and in man it is about 140 g/l of blood (WHO data WHO/LEISH/96.40 appendix 5, page 57). Hence the concentrations used in the invention are preferably about 100 times lower than the physiological concentrations in invertebrates or vertebrates.

The use of at least one globin and/or at least one globin protomer and/or at least one extracellular native hemoglobin avoids the control of the osmotic pressure necessary with the use of red cells. Since the globin, globin protomer and extracellular do not have a blood type, they also make it possible to avoid any problem of immunological reaction encountered with the use of mammalian red cells such as human or bovine hemoglobin contained in blood cells which have different glycan types on their surface responsible for the blood typing. Since the extracellular hemoglobin of *A. marina* is extracellular and non-glycosylated, *A. marina* can be considered as a universal donor.

The organs and tissues are of animal origin, in particular human, or of mammals, birds, reptiles, fish or insects.

A tissue is a group of identical cells or at least of the same origin, participating in a common function. Tissues are grouped into organs.

The expression "storage medium" designates any medium capable of protecting organs and/or cells from the deleterious effects of reperfusion ischemia while satisfying the minimum metabolic needs of the organs and/or cells.

The storage media are aqueous solutions containing electrolytes such as potassium, sodium, magnesium, calcium, chlorine and sulfate and if necessary containing impermeants such as mannitol, raffinose, saccharose, glucose, fructose, lactobionate or gluconate, and can also contain colloids such as albumin, hydroxyethyl starch, polyethylene glycol or dextran 40.

Cell culture media are available commercially and are very diverse. For example, without being restricted thereto, the media available from Invitrogen are the following media: D-MEM, D-MEM/F-12, MEM, RPMI 1640, or medium 199, etc., or any analogous medium.

Examples of solutions, without restricting the invention thereto, are given in table 1 of the thesis of Melle Delphine Fornas (Thesis of Melle Delphine Fornas defended on 15 Jun. 2001: Organ preservation solution: specification, regulatory status and registration in Europe; Université Claude Bernard—Lyon I; Faculty of Pharmacy; Institute of Pharmaceutical and Biological Sciences).

Cell culture should be understood to mean any type of cells, in particular prokaryotic and eukaryotic cells, such as those of free microorganisms (bacteria or yeasts) or "healthy" cells freshly removed from an organism (biopsy, etc.), which then constitute "primary cultures".

It should also be understood to mean cells having an unlimited capacity for division (referred to as "immortality in culture"), for example cancerous cell lines, cells in the process of cancerization, or else healthy cells artificially rendered "immortal".

According to a preferred embodiment of the invention, the globin and/or the globin protomer and or the native hemoglobin defined above is used with an organ storage medium preferably selected from the University of Wisconsin solution (UW, Viaspan®), IGL1®, Celsior®, SCOT Maco®, BMPS Belzer®, Custodiol® (HTK), Euro-Collins®, Soltran®, Perfadex®, Ringer Lactate® or Plegisol®, or any analogous solution.

All these organ storage media are commercial products.

According to another embodiment of the invention, the cell culture defined above corresponds to cells of vertebrates.

Vertebrate designates a mammal, reptile, amphibian, bird or fish.

The cells of vertebrates correspond to any type of cells belonging to a vertebrate animal and can for example, without being restricted thereto, be renal, hepatic, pancreatic, cardiac, pulmonary, intestinal, gastric, colon cells, etc.

According to another embodiment of the invention, the cell culture defined above corresponds to cells of invertebrates.

Invertebrate designates an animal devoid of a vertebral column, for example insects, mollusks, annelids, cnidaria, porifera, etc.

The cells of invertebrates correspond to any type of cells belonging to an invertebrate animal and can for example, without being restricted thereto, be cells of the perivasal/hematopoietic tissue or others.

According to a preferred embodiment, the temperature of the compositions for preservation of organs or cells of organs or cell culture defined above lies between about 4° C. to about 37° C., preferably about 4° C. to about 25° C., more preferably about 4° C. to about 15° C., in particular about 4° C.

Thus the use of at least one globin and/or at least one globin protomer and/or at least one extracellular native hemoglobin makes it possible to produce a composition capable of operating under hypothermic conditions, an essential aspect of storage, since the hypothermia reduces the tissue metabolism, in other words it slows the catalytic enzymatic activity necessary for cell viability.

The use of at least one globin and/or at least one globin protomer and/or at least one extracellular native hemoglobin also makes it possible to cultivate cells of marine invertebrates, which is not possible at present. In fact, primary cultures of marine invertebrates are effected on certain types of invertebrates (some have been maintained for several months), but no cell line has been established (Rinkevich B, Mar Biotechnol (NY). 2005 September-October; 7(5): 429-39).

According to another embodiment, the temperature of the composition for organ perfusion or cell culture lies between about 4° C. to about 37° C., preferably about 15° C. to about 37° C., more preferably about 25° C. to about 37° C., in particular about 37° C.

During the perfusion of an organ, the perfusion temperature must generally be normothermic, in other words close to physiological temperature. Consequently, the use of an extracellular hemoglobin makes it possible to produce a composition also capable of operating under normothermic conditions.

According to another aspect, the invention relates to a composition containing at least one globin and/or at least one globin protomer and/or at least one extracellular native hemoglobin of an invertebrate animal selected from the phylum of the annelids and in particular at least one globin and/or at least one globin protomer and/or at least one extracellular hemoglobin belonging to marine worms such as *Arenicola marina*, at a concentration lying between about 0.625 mg/ml to about 100 mg/ml preferably about 0.625 mg/ml to about 20 mg/ml, more preferably from about 0.625 mg/ml to about 5 mg/ml in particular 1.25 mg/ml, relative to the final volume, and an organ storage medium.

Said composition makes it possible to preserve organs or tissues, or organ or tissue cells, or to perfuse organs or tissues.

According to a preferred embodiment, said organ storage medium is preferably selected from the University of Wisconsin solution (UW, Viaspan®), IGL1®, Celsior®, SCOT Maco®, BMPS Belzer®, Custodiol® (HTK), Euro-Collins®, Soltran®, Perfadex®, Ringer Lactate® or Plegisol®, or any analogous solution, but is not limited only to these colloidal solutions.

According to another aspect, the invention relates to a composition containing at least one globin and/or at least one globin protomer and/or at least one extracellular native hemoglobin of an invertebrate animal selected from the phylum of the annelids and in particular at least one globin and/or at least one globin protomer and/or at least one extracellular hemoglobin belonging to marine worms such as *Arenicola marina*, at a concentration lying between about 0.625 mg/ml to about 100 mg/ml preferably about 0.625 mg/ml to about 20 mg/ml, more preferably from about 0.625 mg/ml to about 5 mg/ml in particular 1.25 mg/ml, relative to the final volume, and a cell culture medium.

Said composition makes it possible to culture cells of vertebrates or invertebrates. According to yet another aspect, the invention relates to a process for storage of organs or tissue, or organ or tissue cells comprising a stage of static or dynamic perfusion storage of said organ in a composition as defined above.

In a preferred embodiment, the process for storage of an organ or tissue, or of organ or tissue cells defined above comprises the following stages:
  removal of said organ or said tissue or said organ or tissue cells;
  rinsing of said organ or said tissue or said organ or tissue cells at a temperature lying between about 4° C. to 37° C., preferably about 4° C. to 25° C., more preferably about 4° C. to about 15° C., in particular about 4° C., with a composition defined above;
  static or dynamic perfusion storage of said organ or said tissue or said organ or tissue cells, at a temperature lying between about 4° C. to 37° C., preferably about 4° C. to 25° C., more preferably about 4° C. to about 15° C., in particular about 4° C., for a defined time, depending on said organ or tissue or said organ or tissue cells, in a composition defined above.

The expression "defined time, depending on said organ or said tissue or said organ or tissue cells" designates a storage time which is specific and depends on the organ used.

The acceptable time to ensure the subsequent resumption of the transplant's function varies from one organ to another. For example, it is about 4-5 hours for the heart, 4-6 hours for the lung, 6 hours for the intestine, 10-16 hours for the liver, 24-35 hours for the kidney and 12-18 hours for the pancreas. All these values are well known to the person skilled in the art and can for example be found in the thesis of Melle Delphine Fornas (Thesis of Melle Delphine Fornas defended on 15 Jun. 2001: Organ preservation solution: specification, regulatory status and registration in Europe; Université Claude Bernard—Lyon I; Faculty of Pharmacy; Institute of Pharmaceutical and Biological Sciences).

According to another aspect, the invention relates to a process for culturing of organ or tissue cells of vertebrates or invertebrates comprising a stage of culturing the cells in a composition as defined above.

According to a preferred embodiment, the process for storage of an organ, defined above, comprises the following stages:
  removal of said organ;
  rinsing of said organ or said tissue or said organ or tissue cells at a temperature lying between about 4° C. to about 37° C., preferably about 15° C. to about 37° C., more preferably about 25° C. to about 37° C., with a composition defined above;
  static or dynamic perfusion storage of said organ at a temperature lying between about 4° C. to about 37° C., preferably about 15° C. to about 37° C., more preferably about 25° C. to about 37° C., in particular about 37° C., for a defined time, depending on said organ, in a composition defined above.

The expression "defined time, depending on said organ" designates a storage time which is specific and depends on the organ used, as indicated above.

According to yet another aspect, the invention relates to a process for culturing cells of vertebrates, comprising the following stages:

removal of said cells from a vertebrate;
culturing at a temperature lying between about 4° C. to 37° C., preferably about 15° C. to about 37° C., more preferably about 25° C. to about 37° C., in particular about 37° C., for a defined time or not, depending on the cells, in a composition defined above;
harvesting of the cells by rinsing and lysis of the cell mat.

The expression "defined time, depending on the cells" designates a culturing time which is specific and depends on the type of cells used, or on the cell line used.

For example, it generally lies between a few hours to about one week for cultures of cells such as blood cells such as polynuclear neutrophils.

These cells cannot normally be maintained in culture indefinitely, in particular because of their limited number of divisions (Hayflick limit).

For primary cultures, cell cultures which are derived directly from a tissue, it normally lies between a few days to several weeks.

This first culture will subsequently be able to give rise to cultures referred to as "secondary", on attain-ment of confluence by the primary culture.

Finally, in the case of immortal cells, this time is not defined and can theoretically be infinite.

In another aspect, the invention relates to a process for culturing cells of invertebrates, comprising the following stages:

removal of said cells from an invertebrate;
culturing at a temperature lying between about 4° C. to 37° C., preferably about 4° C. to about 25° C., more preferably about 4° C. to about 15° C., in particular about 4° C., for a defined time, depending on the cells, in a composition defined above;
harvesting of the cells by rinsing and lysis of the cell mat.

The expression "defined time, depending on the cells" designates a culturing time which is specific and depends on the type of cells used, or on the cell line used.

DESCRIPTION OF DIAGRAMS

FIG. 1 shows the dissociation kinetics of the hemoglobin from *Arenicola marina* (HbAm) in four organ storage media (white square: UW, black circle: IGL1, cross: Celsior, white triangle: BMPS Belzer).

The gray square corresponds to the stability of the hemoglobin of *Arenicola marina* in a buffer used for the purification of the molecule.

Figure 2:
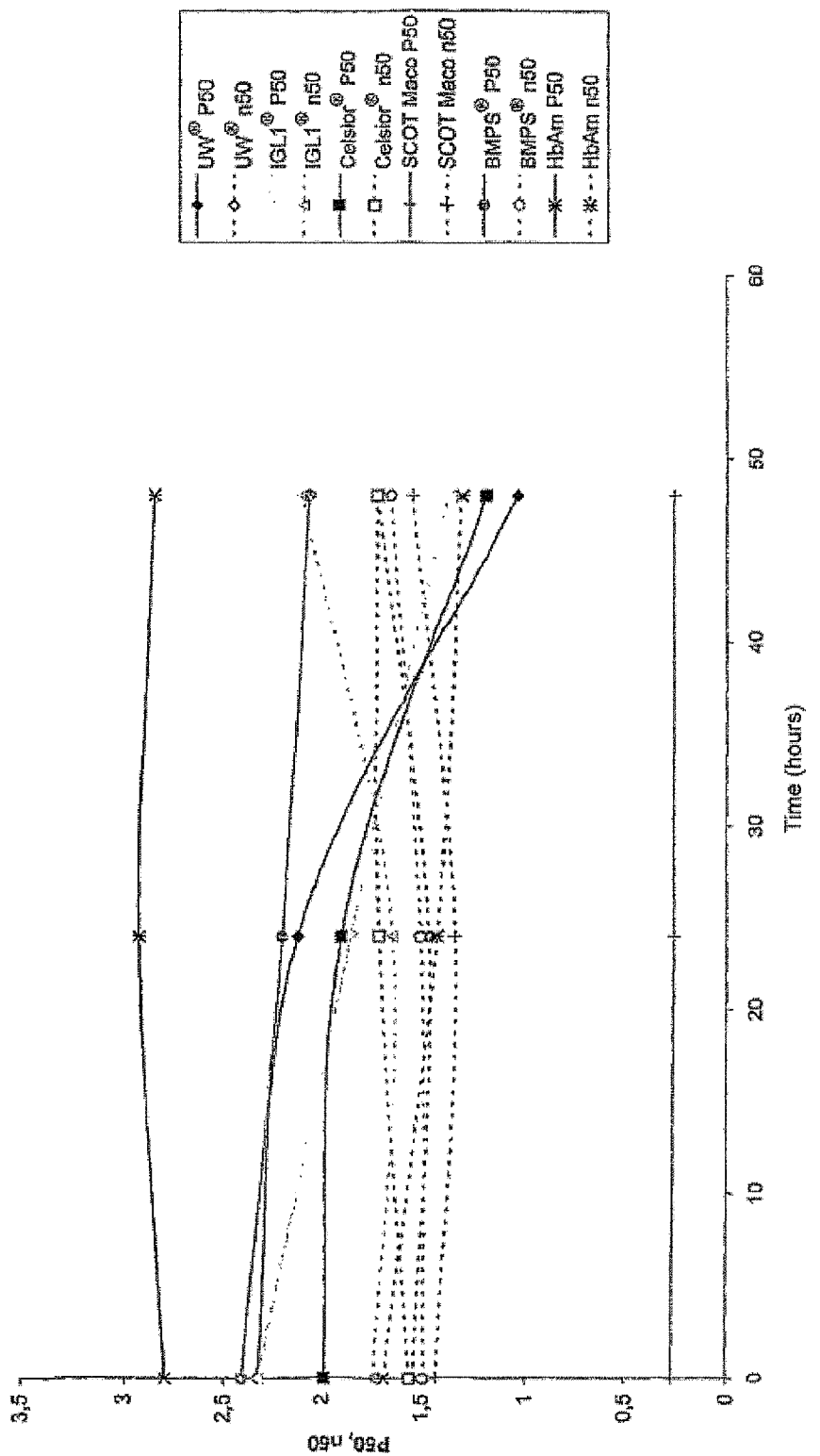

FIG. 2 shows the functional properties of the hemoglobin of *Arenicola marina* (HbAm) in different organ storage media.

For each medium, the measurement of the $P_{50}$ (solid lines) representing the affinity of the hemoglobin of *Arenicola marina* for oxygen and the measurement of the $n_{50}$ (dotted lines) representing the cooperativity are shown.

Figure 3:
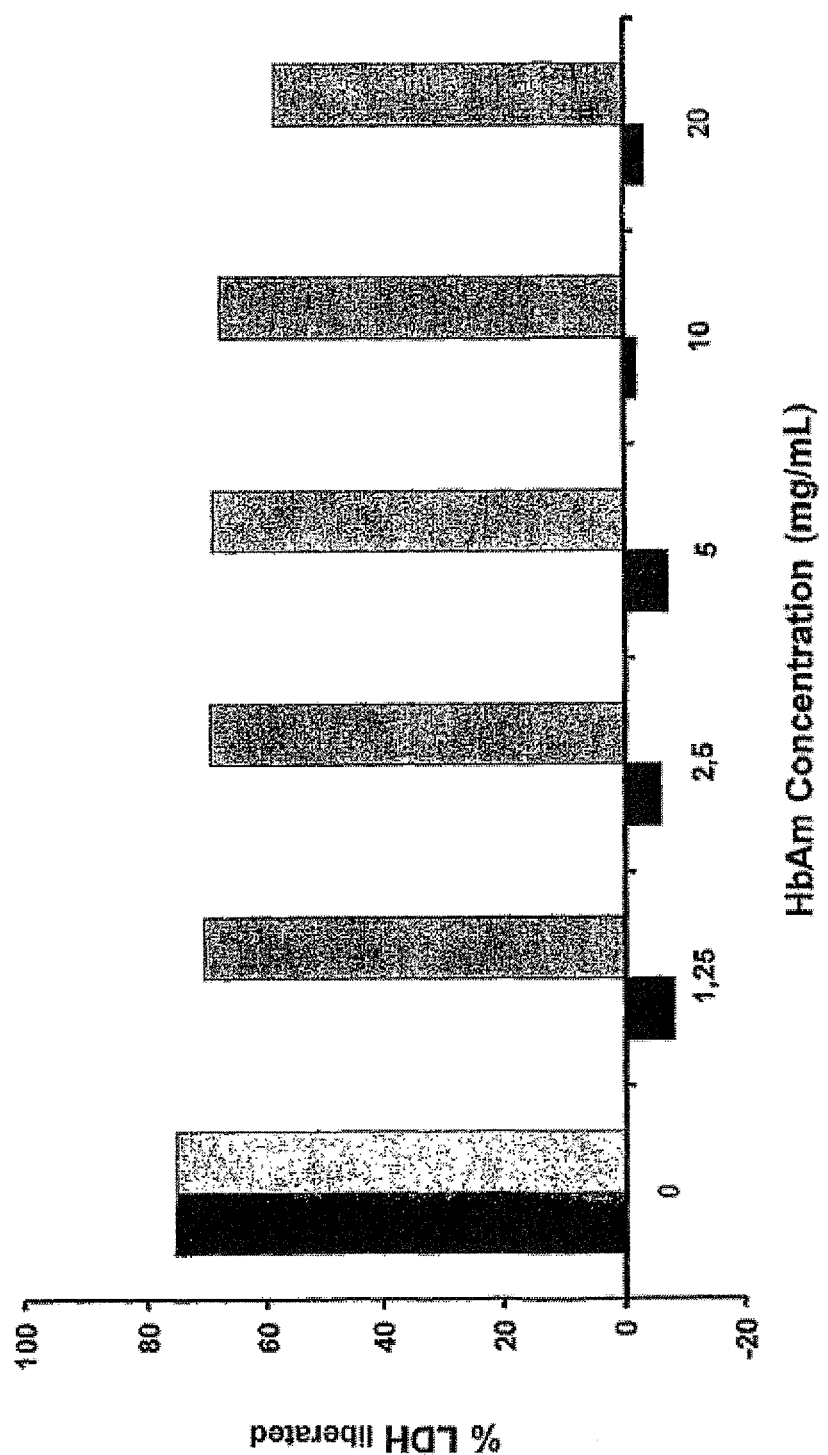

FIG. 3 represents the percentage of lactate dehydrogenase (LDH) liberated in the storage supernatant by the porcine renal tubule cells LLC PK1 (y axis) after 2 hrs at 4° C. as a function of the concentration of *Arenicola marina* hemoglobin (1.25 mg/ml to 20 mg/ml) in an organ storage medium (ViaSpan®, Bristol-Myers Squibb).

The black columns represent the results obtained for the different concentrations of HbAm and the gray columns represent the results obtained with the buffer alone in ViaSpan®, in the absence of HbAm.

Figure 4:
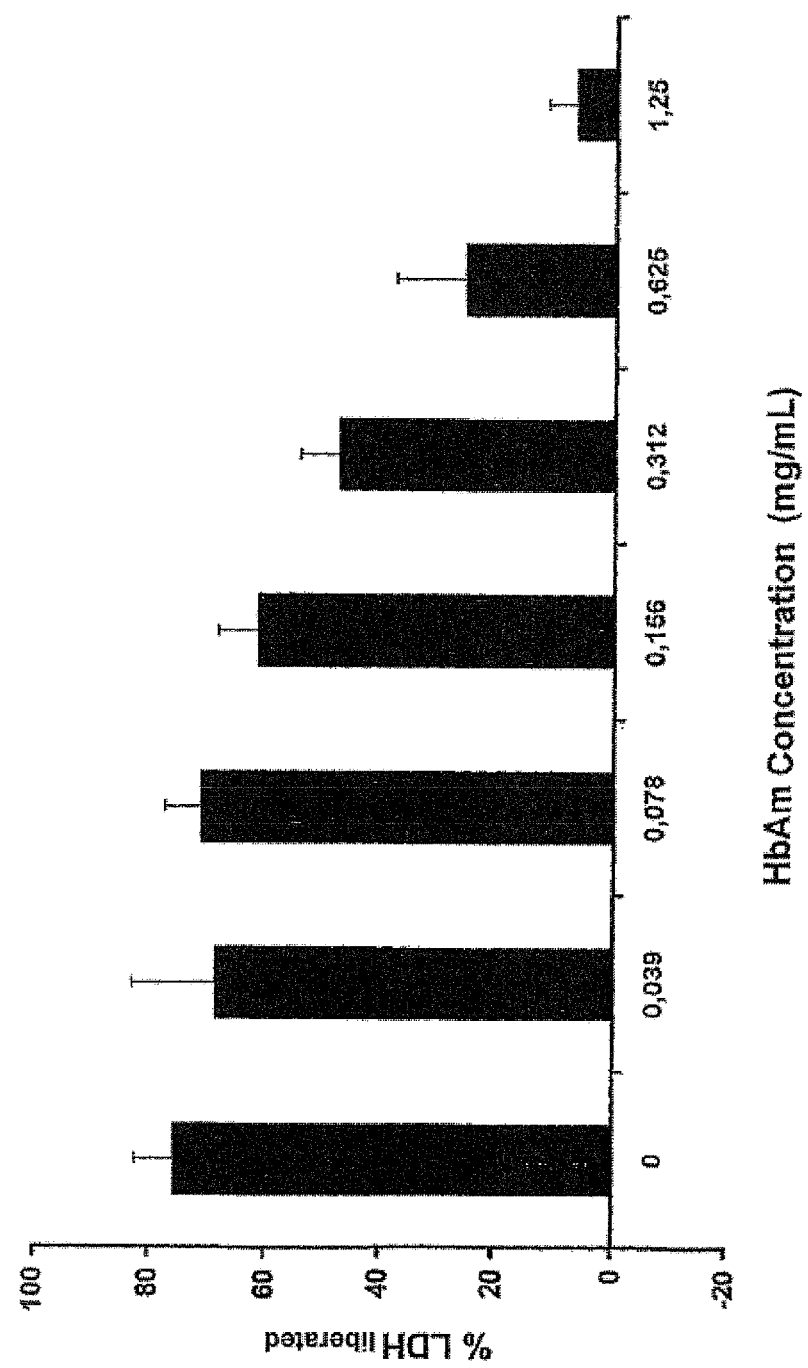

FIG. 4 represents the percentage of detected lactate dehydrogenase (LDH) liberated into the storage supernatant by the porcine renal tubule cells LLC PK1 (y axis) after 24 hrs at 4° C. as a function of the concentration of *Arenicola marina* hemoglobin (0.039 mg/ml to 1.25 mg/ml; x axis) in an organ storage medium (ViaSpan®, Bristol-Myers Squibb).

The black columns represent the results obtained for the different concentrations of HbAm.

EXPERIMENTAL PART

Example 1

Stability of the Hemoglobin of *Arenicola marina* in Different Organ Storage Media These studies were performed in the laboratory in order to evaluate the stability of HbAm in different organ storage media (colloidal solutions currently used during the transplantation of organs and provided by the laboratory of Prof. T. Hauet). These solutions are UW®, IGL1®, Celsior® and BMPS Belzer®.

The kinetic analyses were performed over 48 hrs on the basis of the area under curve of the chromatogram and the percentage of the different subunits at 414 nm (corresponding to the absorbance of heme). The percentage of HbAm as a function of time follows a monoexponential law: $[HbAm]_t/[HbAm]_{t0}=\exp(-k_d t)$, where $k_d$ is the dissociation constant of HbAm.

These studies revealed that in these different organ storage media HbAm is stable, not oxidized and functional for a period of at least 48 hours, which is totally compatible with the lifetime of the organs awaiting transplantation (FIG. 1).

The dissociation constants and the half-lives obtained for the different solutions indicate that HbAm is stable in these different organ storage media tested over 48 hours (dissociation <3%, see table I).

TABLE 1

Dissociation constants and half-lives of HbAm in the different media tested.

|  | HbAm | UW ® | IGL1 ® | Celsior ® | BMPS Belzer ® |
|---|---|---|---|---|---|
| $K_d$ (h$^{-1}$) | 0.0001 | 0.0002 | 0.0011 | 0.0004 | 0.0006 |
| $T_{1/2}$ (h) | ∞ | ∞ | 625 | 1154 | 1705 |

Example 2

Functionality of the Hemoglobin of *Arenicola marina* in Different Organ Storage Media The measurement of $P_{50}$ was effected by the hemox technique (A. Toulmond et al., Biol. Bull. 179 366-373 (1990)) at 4° and for 48 hrs.

The measurement of $n_{50}$ was effected on the oxygen saturation curves of a respiratory pigment, which were obtained using the hemox technique.

The results obtained, presented on FIG. 2, show that HbAm is functional in the different organ storage media tested as is shown by the P50 and n50 values observed (UW, IGL1, Celsior, Scot Maco, BPMS The affinity of HbAm for $O_2$ is strong, lying between 1 and 3 and ca. 0.2 in SCOT Maco. The affinity is slightly greater in the different organ storage media and particularly in SCOT Maco and increases slightly over 48 hours.

The cooperativity is constant at ca. 1.5 between the different storage media and in time.

Example 3

Test of Efficacy of the Hemoglobin of *Arenicola marina* at a Concentration Lying Between 1.25 mg/ml to 20 mg/ml, in an In Vitro Model of Cold Storage of Renal Cells 1) Cold Storage of the Renal Cell Line Biological Material The experiments were performed on the porcine renal tubule cell line LLC-PK1 (CL-101, Lot 1928865) (ATCC, LGC-Promochem, Molsheim, France) kindly provided by the Laboratoire Inserm E0324 "Ischemia-reperfusion in renal transplantation" of Poitiers directed by Prof. G Mauco.

The line LLC-PK1 is a line of non-transformed cells, established from epithelial cells of pig kidney proximal tubules.

Culturing of LLC-PK1 Cells

The LLC-PK1 cells are cultivated in M199 medium (Ref. 31150, Gibco-BrL, Invitrogen Life Technology) supplemented with 3% of fetal calf serum (F7524, lot 085K3397, Sigma-Aldrich), 100 U/ml of penicillin and 100 μg/ml of streptomycin (P4333, Sigma-Aldrich) and mM L-glutamine (25030, Gibco-BrL). The cells are cultivated at 37° C. under a moist atmosphere containing 95% of air and 5% of $CO_2$.

Cold Storage of LLC-PK1 Cells

For the cold storage experiments, the cells are seeded onto 6-well culture plates (140675, Nunc) at a concentration of $2\times10^5$ cells/ml in 2 ml of culture medium for each well. After 48 hrs' culturing, the supernatant is removed and two washings of the cell mat are performed with a saline phosphate buffer (PBS, 70011, Gibco-Brl). The cells are then stored for 24 hrs at 4° C. in the presence of 1.2 ml of a commercial storage solution, the UW solution (ViaSpan®, Bristol-Myers Squibb), to which HbAm had previously been added at concentrations of 0, 1.25, 2.5, 5, 10 or 20 mg/ml.

2) Detection of the Liberation of Lactate Dehydrogenase (LDH)

The impact of the addition of HbAm stored in Hemorgan holding buffer on the viability of the LLC-PK1 cells stored for 24 hrs at 4° C. in the UW solution was studied. The cell viability was studied by detection of the quantity of LDH present in the cell mat after cold storage in comparison to the quantity of LDH initially present in the mat before the storage stage.

In fact, the liberation of this enzyme into the extracellular medium is a reflection of the permeabilization of the plasmic membrane of the cells and hence of cell death.

Method

After 24 hrs' storage, the supernatant is removed and the cell mat is then rinsed 3 times with 2 ml of PBS then the adherent cells are lysed in 1.2 ml of PBS containing 0.1% of Triton® X-100 (X100, Sigma-Aldrich). The suspension obtained after scraping out the cell mat is sonicated for 10 secs with an ultrasound device then centrifuged at 1,000 g for 7 mins.

The quantity of LDH present in the cell mat is determined by a colorimetric assay according to the manufacturer's instructions (TOX7, Sigma-Aldrich). This assay is based on the reduction of NAD by the LDH during the transformation of pyruvate into lactate. In short, 25 μl of the sample to be assayed are placed in a 96-well plate before the addition of 25 μl of a reaction mixture containing 1 volume of substrate (L2402), 1 volume of cofactor (L2527) and 1 volume of colorant (L2277). The mixture is then homogenized gently and incubated for 5 mins at ambient temperature in the dark. The reaction is stopped by addition of 5 μl of 1N HCl. The absorbance measured by photometry at 490 nm and 630 nm (plastic reference) (ELx800™, Biotek coupled to the Gen5® software) is directly proportional to the quantity of enzyme present in the sample. Each sample is assayed in duplicate and a mean is taken of the difference in absorbance (OD490-OD630).

Results

The results are expressed as a percentage of the quantity of LDH detected in the cell mat stored at 4° C. relative to the quantity of LDH detected in the mat before the cold storage period (cells at T0). The percentage LDH liberation is then calculated from the relationship:

$$100-[(\text{cell mat LDH})\times 100/(\text{LDH cells at } T0)]$$

(FIG. 3 and table II).

TABLE II

Percentage LDH liberation obtained for the different concentrations of HbAm or in buffer (the results correspond to the mean of three runs).

| HbAm | UW | 1.25 g/L | 2.5 g/L | 5 g/L | 10 g/L | 20 g/L |
|---|---|---|---|---|---|---|
| MEAN | 74 | −6 | −3 | −3 | −2 | −5 |
| S.D. | 9 | 6 | 4 | 8 | 4 | 2 |
| Tp Am | UW | 25 μL | 50 μL | 100 μL | 200 μL | 300 μL |
| MEAN | 74 | 72 | 69 | 72 | 70 | 62 |
| S.D. | 9 | 5 | 6 | 3 | 5 | 4 |

Conclusion

Storage of LLC-PK1 cells in the UW solution (ViaSpan) for 24 hrs at 4° C. induces considerable cell death (74±9%).

Further, the presence of the holding buffer Hemorgan in the UW storage solution causes little or no change in the viability of the renal cells.

In contrast, the presence of HbAm during storage, and this from a concentration of 1.25 g/l of the substance, totally protects the viability of the cell mat.

Example 4

Test of Efficacy of the Hemoglobin of *Arenicola marina* at a Concentration Lying Between 0.039 mg/ml and 1.25 mg/ml, in an In Vitro Model of Cold Storage of Renal Cells The biological material, cell culture and cold storage are prepared and effected in the same manner as in example 3.

Concentrations of HbAm

The cells are stored for 24 hrs at 4° C. in the presence of 1.2 ml of a commercial storage solution, UW solution (ViaSpan®, Bristol-Myers Squibb), to which HbAm has previously been added at concentrations of 0, 0.039, 0.078, 0.156, 0.312, 0.625 or 1.25 mg/ml.

Results

The results are expressed as a percentage of the quantity of LDH detected in the cell mat stored at 4° C. relative to the quantity of LDH detected in the mat before the cold storage period (cells at T0). The percentage LDH liberation is then calculated from the relationship:

$$100-[(\text{cell mat LDH})\times 100/(\text{LDH cells at } T0)]$$

(FIG. 4 and table III).

TABLE III

Percentage LDH liberation obtained for the different concentrations of HbAm (the results correspond to the mean of three runs).

| HbAm | UW cel | 0.039 g/L C | 0.078 g/L | 0.156 g/L | 0.312 g/L | 0.625 g/L | 1.25 g/L |
|---|---|---|---|---|---|---|---|
| MEAN | 76 | 69 | 71 | 62 | 47 | 25 | 7 |
| S.D. | 7 | 14 | 6 | 7 | 7 | 12 | 5 |

Conclusion

Storage of LLC-PK1 cells in the UW solution (ViaSpan) for 24 hrs at 4° C. induces considerable cell death (76±7%). The liberation of LDH from the renal tubule cells is markedly reduced in the presence of HbAm and this is dose-dependent. Thus, from 0.625 mg/ml HbAm protects the renal cells (25±12% versus 76±7%) and at a concentration of 1.25 g/l HbAm totally protects the renal cells from the cell death induced by 24 hrs of cold storage (7±5% versus 76±7%).

The invention claimed is:

1. A method for the preservation of organs, tissues, or organ cells comprising perfusing said organs, tissues, or organ cells with a composition comprising at least one globin and/or at least one globin protomer and/or at least one naturally extracellular native hemoglobin of an invertebrate animal selected from a marine worm of the phylum Annelida, in combination with an organ storage medium, said medium being capable of protecting said organs, tissues, or cells from the deleterious effects of ischemia while satisfying the minimum metabolic needs of said organs, tissues, or cells wherein said marine worm is *Arenicola marina*.

2. The method of claim 1, characterized in that the organ storage medium is selected from the group consisting of University of Wisconsin solution (UW, Viaspan®), IGL 1®, Celsior®, SCOT Maco®, BMPS Belzer®, Custodiol® (HTK), Euro-Collins®, Soltran®, Perfadex®, Ringer Lactate®, and Plegisol®.

3. The method of claim 1, wherein said tissues or organ cells comprise vertebrate cells.

4. The method of claim 1, wherein said tissues or organ cells comprise invertebrate cells.

5. The method of claim 4, wherein the temperature of the composition is from about 4° C. to about 15° C.

6. The method of claim 1, wherein the temperature of the composition is from about 4° C. to about 15° C.

7. The method of claim 1, wherein the temperature of the composition is from about 25° C. to about 37° C.

8. The method of claim 1, wherein the at least one globin and/or at least one globin protomer and/or at least one naturally extracellular native hemoglobin is at a concentration of about 0.625 mg/ml to about 100 mg/ml, relative to the final volume of the composition.

9. A process for storage of organs, tissues, or organ cells, the process comprising static or dynamic perfusion storage of said organs, tissues, or cells comprising:
perfusing said organs, tissues, or cells with a composition comprising at least one globin and/or at least one globin protomer and/or at least one naturally extracellular native hemoglobin of an invertebrate animal selected from a marine worm of the phylum Annelida, in combination with an organ storage medium, said medium being capable of protecting said organs, tissues, or cells from the deleterious effects of ischemia while satisfying the minimum metabolic needs of said organs, tissues, or cells wherein said marine worm is *Arenicola marina*.

10. The process of claim 9, further comprising:
rinsing of said organ, tissue, or organ cells, previously removed from an organism, with said composition at a temperature of about 4° C. to about 15° C.; and
performing the static or dynamic perfusion storage at a temperature of about 4° C. to about 15° C., for a defined time.

11. The process of claim 9 further comprising:
rinsing of said organ, previously removed from an organism, at a temperature of about 25° C. to about 37° C. with said composition; and
performing the static or dynamic perfusion storage of said organ with said composition at a temperature of about 25° C. to about 37° C. for a defined time.

12. The method of claim 9, wherein the at least one globin and/or at least one globin protomer and/or at least one naturally extracellular native hemoglobin is at a concentration of about 0.625 mg/ml to about 100 mg/ml, relative to the final volume of the composition.

13. A process for culturing organ cells or organ tissues of vertebrates or of invertebrates, the process comprising culturing said tissues or cells in the presence of a composition comprising at least one globin and/or at least one globin protomer and/or at least one naturally extracellular native hemoglobin of an invertebrate animal selected from a marine worm of the phylum Annelida, in combination with an organ storage medium or a cell culture medium, said medium being capable of protecting said tissues or cells from the deleterious effects of ischemia while satisfying the minimum metabolic needs of said tissues or cells wherein said marine worm is *Arenicola marina*.

14. The process of claim 13, comprising:
culturing organ cells at a temperature from about 25° C. to about 37° C., for a defined time; and
harvesting the cells by rinsing and lysing the cells.

15. The process of claim 13, comprising:
culturing organ cells at a temperature from about 4° C. to about 15° C., for a defined time; and
harvesting the cells by rinsing and lysing the cells.

16. The method of claim 13, wherein the at least one globin and/or at least one globin protomer and/or at least one naturally extracellular native hemoglobin is at a concentration of about 0.625 mg/ml to about 100 mg/ml, relative to the final volume of the composition.

* * * * *